United States Patent [19]

Manziek

[11] 4,240,909

[45] Dec. 23, 1980

[54] BORANE REDUCING RESINS FOR REMOVAL OF METAL IONS

[75] Inventor: Larry Manziek, Horsham, Pa.

[73] Assignee: Rohm and Haas Company, Philadelphia, Pa.

[21] Appl. No.: 886,221

[22] Filed: Mar. 13, 1978

Related U.S. Application Data

[62] Division of Ser. No. 749,560, Dec. 10, 1976.

[51] Int. Cl.³ .................... B01D 15/00; C02F 1/70
[52] U.S. Cl. .................... 210/688; 210/721; 210/735
[58] Field of Search ............. 75/89, 101 BE, 108, 75/109; 210/24 R, 28, 36, 37 B, 38 B, 42 R, 50, 54; 260/583 A, 606.5 B; 526/24

[56] References Cited

U.S. PATENT DOCUMENTS

| | | | |
|---|---|---|---|
| 2,683,721 | 7/1954 | Schlesinger | 260/343.3 R |
| 2,709,704 | 5/1955 | Brown | 260/347.8 |
| 2,731,454 | 1/1956 | Edmonds | 528/392 |
| 2,856,428 | 10/1958 | Brown | 260/570.9 |
| 2,874,165 | 2/1959 | Brown | 260/343.6 |
| 2,944,084 | 7/1960 | Blitzer | 260/606.5 R |
| 2,945,886 | 7/1960 | Brown | 260/570.9 |
| 2,954,276 | 9/1960 | Hazen | 210/28 |
| 3,520,865 | 7/1970 | Pampus | 526/24 |
| 3,531,463 | 9/1970 | Gustafson | 210/30 R |
| 3,609,191 | 9/1971 | Wade | 260/583 A |
| 3,647,890 | 3/1972 | Kreevoy | 568/809 |
| 3,679,646 | 7/1972 | Bristol | 526/7 |
| 3,928,293 | 12/1975 | Crosby | 260/606.5 B |
| 3,978,140 | 8/1976 | Lane | 568/705 |
| 4,029,706 | 6/1977 | Crosby | 260/570.9 |
| 4,078,002 | 3/1978 | Brown | 260/583 K |
| 4,080,381 | 3/1978 | Burke et al. | 252/188 |

FOREIGN PATENT DOCUMENTS 876034  8/1961  United Kingdom .

OTHER PUBLICATIONS

Hallensleben, "Prep. of Poly(4-Vinylpyridine Borane)", J. Polymer Science, Sympos, No. 47, pp. 1-9, 1974.

Davis et al., "Methanolysis of Sodium Borohydride", J. A. C. S. 84, pp. 895-898, 3/1962.

Regen et al., "Solid Phase Phosphorus Reagents", J. Org. Chem., 40, No. 11, 1975, pp. 1669-1670.

*Primary Examiner*—Charles N. Hart
*Assistant Examiner*—Peter A. Hruskoci
*Attorney, Agent, or Firm*—Bernard J. Burns; George W. F. Simmons; Robert A. Doherty

[57] ABSTRACT

This invention relates to solid nonionic crosslinked resins containing amine or phosphine borane adducts and their use as reducing agents for metal ions.

10 Claims, No Drawings

BORANE REDUCING RESINS FOR REMOVAL OF METAL IONS

This is a division of application Ser. No. 749,560 filed Dec. 10, 1976.

BACKGROUND OF THE INVENTION

It is known in the art, [see M. L. Hallensleben, *J. Polymer Science:* Symposium No. 47, 1-9 (1974)], that linear and cross-linked copolymers of 4-vinylpyridine borane, 4-vinylpyridine, and styrene can be prepared and used as polymeric reducing agents for aldehydes and ketones. It is also reported in the literature, [see E. Cernia and F. Gaspuarini, *J. Applied Polymer Science,* vol. 19, 917-20 (1975)], that 4-vinylpyridine borane hydride polymers rapidly decompose in aqueous solutions of strong mineral acids and can only be used as reducing agents for aldehydes and ketones at or about neutral pH.

U.S. Pat. No. 3,928,293 granted Dec. 23, 1975 discloses solid cross-linked thiohydrocarbon borane hydride polymers and their use as reducing agents for aldehydes ketones, lactones, oxides, esters, carboxylic acids, nitriles and olefins. These borane polymers although stabile at room temperature can release borane ($BH_3$) under conditions of reduced pressure or heat and are disclosed as being useful as a convenient means of storing borane. U.S. Pat. No. 3,609,191 granted Sept. 28, 1971 discloses polyethylene imine borane complexes which are stable toward hydrolysis at a pH as low as 5.0. These compositions are useful as reducing agents in chemical plating baths for nickel, copper and silver in a pH range of 5 to 8. However, these products are viscous or solid polymers which range in water solubility from completely soluble to slightly soluble depending on the ratio of $BH_3$ to amino groups in the polymer. The use of ion-exchange resins to extract heavy metals from aqueous solutions via ion-exchange mechanisms is also reported in the art.

SUMMARY OF THE INVENTION

This invention relates to a novel process of reducing metal ions by using nonionic cross-linked resins containing amine or phosphine borane adducts of the formula

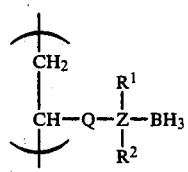
(I)

wherein Q is a group of the formula $$-(CH_2)_{\overline{m}}-T-(CH_2)_n-$$

wherein
m and n are independently integers from 0 to 3; and
T is the group

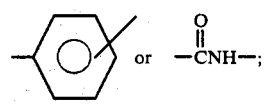

and $R^1$ and $R^2$ are independently
(a) hydrogen;
(b) ($C_1$–$C_8$) optionally substituted alkyl;
(c) ($C_6$–$C_{12}$) optionally substituted aryl; and
(d) ($C_7$–$C_{12}$) optionally substituted aralkyl; and Z is nitrogen or phosphorus, and their use as highly selective reducing agents and as starting materials for the preparation of novel metal catalysts for use in hydrogenation reactions.

The term "alkyl" as utilized in the present specification and claims is meant to include both straight and branch chained alkyl groups which can be optionally substituted with up to three substituents, preferably with up to two substituents, more preferably with up to one substituent, selected from the group consisting of hydroxy, mercapto, fluoro, chloro, bromo, iodo, nitro, methoxy, ethoxy, isopropoxy, amino, methylamino, dimethylamino, ethylamino, diethylamino, amido, methylamido and dimethylamido.

The term "aryl" as utilized in the present specification and claims is meant to include aryl groups such as phenyl, naphthyl and biphenyl, which can be optionally substituted with up to three substituents, preferably with up to two substituents, more preferably with up to one substituent, selected from the group consisting of fluoro, chloro, bromo, iodo, nitro, methyl, ethyl, methoxy, ethoxy and trihalomethyl.

The term "aralkyl" as utilized in the present specification and claims is meant to include such aralkyl groups as benzyl, phenethyl, phenylpropyl, naphthylmethyl and naphthylethyl which can be optionally substituted with up to three substituents, preferably with up to two substituents, more preferably with up to one substituent, selected from the group consisting of fluoro, chloro, bromo, iodo, nitro, methyl, ethyl, methoxy, ethoxy and trihalomethyl.

The preferred nonionic borane resins of this invention are those wherein T is the group

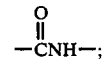

Z is nitrogen; and $R^1$ and $R^2$ are independently hydrogen, ($C_1$–$C_8$) unsubstituted alkyl, ($C_6$–$C_{12}$) unsubstituted aryl or ($C_7$–$C_{12}$) unsubstituted aralkyl.

The more preferred nonionic borane resins of this invention are those where T is the group

Z is nitrogen; and $R^1$ and $R^2$ are independently hydrogen, ($C_1$–$C_4$) unsubstituted alkyl or unsubstituted phenyl, biphenyl, benzyl or phenethyl.

DETAILED DESCRIPTION OF THE INVENTION

The solid nonionic cross-linked borane reducing resins of this invention are highly selective reducing agents which are particularly useful in selectively reducing at room temperature, from both aqueous and non-aqueous media, mercury, silver, gold, platinum, palladium, rhodium, iridium, antimony, arsenic and bismuth ions; to the exclusion of copper, nickel, zinc, iron, lead, tin, cadmium, vanadium, chromium, uranium, thorium, cobalt, thallium, aluminum and the Group I and II members of the Periodic Table. These resins reduce the metal ions in solution via electron transfer and precipitate the reduced metals on and/or into the resin.

These borane resins are capable of being utilized over a wide range of pH conditions and can be utilized at pH ranges greater than about 1.0 but less than about 8.0. These resins are preferably utilized at pH ranges of from about 2.0 to about 4.0. These borane resins are not only stabile in acidic and basic media but are also air stabile as well.

The solid nonionic cross-linked borane reducing resins can also be utilized as reducing agents for aldehydes, ketones, olefins and other functional groups capable of undergoing hydroboration reactions. These reagents reduce the aldehydes, ketones, olefins and the like via hydride transfer and the resultant product can be liberated from the resin via strong acid hydrolysis. An added feature of this reduction procedure is the ability of these resins to concentrate the products onto the resin thereby effecting a concentration and a purification of the products formed before hydrolyzing them off the resin. Although the macroreticular form of the resin is preferred, the gel form or any other particulate form of the nonionic borane reducing resins of the present invention can be utilized as reducing agents.

The reduced metals which are precipitated on and/or into the nonionic borane reducing resins of the present invention can be either dissolved out of the resin via strong acid or in the case of mercury can be withdrawn by treatment with hot water. The more preferred method of obtaining the reduced precious metals from the resins is by burning the resin away from the metals since the value of the precious metals far exceeds the cost of the resin.

These nonionic borane reducing resins have an advantage over ion exchange resins in that ion exchange resins have distinct leakage problems due to the various ion exchange equilibrium for each specific metal ion and ion exchanger. There is no such leakage problem due to ion exchange equilibrium kinetics in the nonionic borane reducing resins of the present invention. These resins reduce the metals to their zero oxidation state and precipitate them on and/or into the resin. Another advantage of these resins and in particular of the macroreticular resins is their ability to contain large capacities of reduced metals before breakthrough finally occurs.

The solid nonionic cross-linked amine and phosphine borane reducing resins can also be utilized as starting materials for the preparation of novel metal catalysts for use in hydrogenation reactions. The resultant metal containing resins can either be pyrolyzed to give a carbon-metal reduction catalyst or they can be combusted in the presence of oxygen to give the metal in a bead form. Moreover, catalysts containing known percentages of metals or of mixed metals can be formed via this process. The nonionic borane reducing resins of the present invention can be prepared by the following general synthetic routes.

In the preparation of the nonionic borane reducing resins of the present invention a suitable water insoluble cross-linked resin having a functional group of the formula

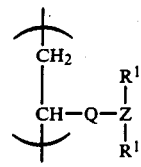

(II)

wherein Q, $R^1$, $R^2$ and Z are as defined in Formula (I) above is reacted with a suitable protonating mineral acid such as hydrohalic, phosphoric, sulfuric and the like, preferably hydrochloric acid to form the cationic group of the formula

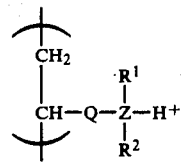

(III)

This reaction is carried out in either a batch or column process at temperatures from about 0° to about 100° C., preferably at about 20° C., in a suitable protic solvent preferably water. The amount of protonating acid used can be anywhere from 5% of the equivalents of weak base in the resin to any percentage over and above the equivalents of weak base in the resin, but is preferably utilized in a 25% excess over the equivalents of weak base in the resin. After the protonation step has taken place the resin is then treated with a water wash to remove any excess acid and then washed thoroughly with a suitable drying solvent such as methanol, ethanol, propanol, acetone, dimethylformamide and the like or alternatively can be air or vacuum dried. In a more preferred process for this protonation step the reaction is carried out in a batch process and a stoichiometric amount of acid is added to protonate all the available protonizable groups. Longer reaction times are preferred in this process since it allows complete diffusion of the acid throughout the resin beads. The borane is preferably incorporated into the protonated resin by treating the resin either in a column or batch process with an excess of a solution of lithium, sodium or potassium borohydride dissolved in an appropriate solvent such as methanol, ethanol, dimethylformamide, monoglyme, diglyme and the like at temperatures from about 0° to about 150° C. preferably at about room temperature.

Another method for incorporating the borane into the resin is by directly treating the amine or phosphine functionality with diborane gas either in a column or batch process or with a solution of diborane in an appropriate solvent such as diethyl ether, tetrahydrofuran, and the like at temperatures from about 0° to about 150° C. preferably at about room temperature.

Those resins which contain amide functions either in the T, $R^1$, or $R^2$ groups can be converted into amines via the use of excess borohydride reagent thereby reducing the bulk and increasing the ratio of the amount of borane to the amount of resin.

In the preparations where less than an equivalent of borohydride or diborane is utilized a mixed cationic and nonionic boraine reducing agent is obtained which would remove metal complex anions and metal cations by both anionic exchange and by reduction of the metal cation or metal complex anion by the borane to the zero oxidation state.

Suitable cross-linked resins which can be utilized in the preparation of the nonionic borane reducing resins of this invention are those described in U.S. Pat. No. 2,675,359 granted Apr. 13, 1974; U.S. Pat. No. 3,037,052 granted May 29, 1962; U.S. Pat. No. 3,531,463 granted Sept. 29, 1970; and U.S. Pat. No. 3,663,467 granted May 16, 1972. The procedures described in these patents for making the cross-linked resins in both the gel and macroreticular form which are contained therein are all incorporated herein by reference.

The following examples are provided to illustrate the preparation of the nonionic borane reducing resins of the present invention and are not to be considered in any way as limitations on the breadth and scope thereof.

EXAMPLE I

Synthesis of the acrylic based amine-borane reducing resin

Step A. Protonation

A sample (50.0 g) of an acrylic based, macroreticular, weak base resin having a weak base capacity of 5.4 meq. of weak base per gram of dry resin is stirred with an aqueous hydrochloric acid solution containing 360 meq. of hydrochloric acid (30% excess) for 5 hours. The resin is washed with deionized water to a neutral pH, then with two 300 ml portions of acetone and then vacuum dried at 50° C. for 8 hours. Yield, 59.9 grams.

Step B. Borane Addition

To a 500 ml round bottom three neck flask equipped with a sealed mechanical stirrer, pressure compensating dropping funnel and mineral oil bubbler, is added a sample (52.8 g, 238.1 meq of H+) of a dried acrylic based, macroreticular weak base resin (in the hydrochloride form) containing 4.51 meq of H+ per gram of dry resin. A solution of sodium borohydride (10.0 g, 97% purity, 256 meq., 7% excess) in 250 ml of dry N,N-dimethylformamide is added rapidly with continuous stirring. The mixture is stirred at room temperature until no further hydrogen gas evolution is observed. The N,N-dimethylformamide is removed by filtration and the remaining resin is backwashed with deionized water until no chloride ion is detectable with silver nitrate and the pH is approximately seven. The resin is then vacuum dried at 30° C.

EXAMPLE II

Synthesis of the polystyrene based amine-borane reducing resin

Step A. Protonation

Utilizing the procedure in Example I Step A and a polystyrene based, macroreticular, weak base resin the desired intermediate protonated product is obtained.

Step B. Borane Addition

Utilizing the procedure in Example I Step B and a protonate polystyrene based, macroreticular, weak base resin the desired borane addition product is obtained.

EXAMPLE III

Synthesis of polystyryl-diphenylphosphine-borane reducing resin

Step A. Preparation of polystyryl-diphenylphosphine

Utilizing the procedures in J. Org. Chem. Vol. 40, No. 11, p. 1669 (1975) the macroreticular form of the polystyryl-diphenylphosphine is prepared.

Step B. Borane Addition

A sample of macroreticular polystyryl-diphenylphosphine (10.0 g., 5.0 meq phosphine/gram) is allowed to react with a tetrahydrofuran solution containing diborane (100 ml, 50 meq. $BH_3$). The mixture is stirred at room temperature for 3 hours. The resulting resin is washed with tetrahydrofuran and is vacuum dried.

EXAMPLE IV

Iodine Determination of Borane Concentration in Borane Reducing Resins

The presence and amount of borane functionality is determined by the reaction of the resin with an aqueous iodine solution and titration of excess iodine with a standardized solution of sodium thiosulfate. In this determination it is imperative that the amount of iodine adsorbed by the resin matrix be calculated for the blank. Thus, the amount of iodine reduced by the borane functionality is equal to the total amount of iodine removed minus the amount adsorbed by the polymer. This adsorption blank approach is only valid for borane resins containing borane concentrations approaching the theoretical amount i.e. all weak base sites coordinated with borane.

EXAMPLE V

Reduction of Cyclohexanone to cyclohexanol with amine-borane resin in aqueous or non-aqueous media Samples of acrylic amine-borane and styrene based amine borane resins as well as their weak base analogs from which they are derived are exposed to both aqueous and tetrahydrofuran solutions of cyclohexanone of known concentration (4%) for a period of two hours. During this time no reaction of the cyclohexanone is observed as evidenced by a chromatographic determination of its original concentration. To each sample is added an amount of acid, HCl for the aqueous system and $BF_3$ for the tetrahydrofuran; in an amount equivalent to the concentration of the cyclohexanone. Both amine-borane resins revealed an immediate decrease in the concentration of cyclohexanone. The formation of cyclohexanol is observed in the aqueous system. However, no cyclohexanol is observed in the tetrahydrofuran solution which is to be expected in the presence of $BF_3$ which would complex the alcohol. The loss of cyclohexanone is however indicative of the reaction of the amine borane resin with cyclohexanone.

EXAMPLE VI

Batch equilibrium capacities for several precious metals

Batch equilibrium capacities are determined by reacting a known amount of amine-borane resin with an aqueous solution of the metal ion under investigation for a period of 16 hours with continuous shaking. The initial and final concentrations of the metal ion are determined by atomic absorption spectroscopy and capacities calculated from the difference.

Samples of amine-borane resin are reacted with aqueous solutions of $AuCl_4^-$, $PdCl_4^{-2}$, and $PtCl_6^{-2}$ of known concentration according to the above procedure. The results are listed in the following table.

| Amine-borane resin weight in grams | Metal Ion | Initial Conc. grams | Final Conc. grams | Capacity g metal/gram |
|---|---|---|---|---|
| 0.1090 | $AuCl_4^-$ | 0.315 | 0.0705 | 2.25 |
| 0.1020 | $PtCl_6^{-2}$ | 0.322 | 0.122 | 1.96 |
| 0.1020 | $PdCl_4^{-2}$ | 0.194 | 0.076 | 1.16 |

EXAMPLE VII

Precious metal recovery by combustion

Recovery of the metal from the metal filled beads is easily accomplished by burning the resin matrix away under an oxygen atomosphere.

A sample of gold filled resin (3.004 g) is combusted at 800° C. for 30 minutes in a furnace. Bright colored metalic gold beads are recovered (1.646 g) corresponding to an initial weight percent of 55%. The beads appear as uniform spheres possessing rough surfaces. Similar results are obtained from palladium and platinum filled resins under identical conditions.

EXAMPLE VIII

Catalyst formations

Samples (1.00 g) of palladium or platinum filled beads are pyrolyzed at 600° C. under a stream of nitrogen for 30 mins. The resulting spherical beads appear as carbon spheres of high density attributed to the presence of the metal.

EXAMPLE IX

Metal reducing selectivity

The amine-borane resin reactivity for various metals is determined by placing a sample (0.10 g) in a vial and adding a concentrated solution of the metal ion or complex under investigation. The vial is allowed to stand for 3 weeks to ensure sufficient contact time. Reaction is confirmed by either a visible change in the beads such as a darkening in color, an increase in weight of the beads when washed with DI water and vacuum-dried, or their inability to further reduce solutions of $AuCl_4^-$. Likewise a positive reduction of $AuCl_4^-$ indicates that no reaction with the metal ion under investigation has occured. The following table represents those metals investigated and their ability to be reduced.

| Metal ion | Source | Not Reduced | Reduced |
|---|---|---|---|
| $Na^+$ | NaCl | — | |
| $K^+$ | KCl | — | |
| $Li^+$ | LiCl | — | |
| $Mg^{+2}$ | $MgCl_2$ | — | |
| $Ca^{+2}$ | $CaCl_2$ | — | |
| $Cr^{+3}$ | $CrCl_3$ | — | |
| $Cr^{+6}$ | $K_2Cr_2O_6$ | — | |
| $UO_2^+$ | $UO_2NO_3$ | — | |
| $Bi^{+3}$ | $Bi(NO_3)_3$ | — | |
| $As^{+3}$ | $As_2O_3$ | — | |
| $Mn^{+2}$ | $MnCl_2$ | — | |
| $Fe^{+2}$ | $FeCl_2$ | — | |
| $Fe^{+3}$ | $FeCl_3$ | | — |
| $Co^{+2}$ | $CoCl_2$ | — | |
| $Ni^{+2}$ | $NiCl_2$ | — | |
| $Cu^{+2}$ | $CuCl_2$ | | — |
| $Zn^{+2}$ | $ZnCl_2$ | — | |
| $Rh^{+3}$ | $RhCl_3$ | | — |
| $Pd^{+2}$ | $PdCl_2$ | | — |
| $Ag^{+1}$ | $AgNO_3$ | | — |
| $Cd^{+2}$ | $CdCl_2$ | — | |
| $Ir^{+3}$ | $IrCl_3$ | | — |

-continued

| Metal ion | Source | Not Reduced | Reduced |
|---|---|---|---|
| $Pt^{+4}$ | $H_2PtCl_6$ | | — |
| $Au^{+3}$ | $HAuCl_4$ | | — |
| $Hg^{+2}$ | $HgCl_2$ | | — |
| $Sb^{+3}$ | $Sb_2O_3$ | | — |
| $Sr^{+2}$ | $SrCl_2$ | — | |
| $Pb^{+2}$ | $PbCl_2$ | | — |
| $Tl^{+1}$ | $Tl_2(SO_4)$ | | — |
| $Pb^{+4}$ | $Et_4Pb$ | | — |
| $CH_3Hg^+$ | $CH_3HgCl^-$ | | — |

EXAMPLE X

Analytical determination of gold

A gold solution containing 5 ppm $Au^{+3}$ (1000 ml) is allowed to react with a sample of the amine-borane resin in a column operation under very slow flows (0.5 ml/min). After loading is completed the resin is assayed for gold and it was determined that a quantitative amount of gold is present; thus, establishing the resins utility as an analytical method for determining trace amounts of gold or other reactive trace metals.

The non-ionic borane reducing resins of this invention can be utilized in either batch or column operations and in addition to their use as reducing agents for metals, aldehydes, ketones and olefins can also be utilized as an analytical reagent. These resins can be used to detect microquantities of metal ions in various aqueous and non-aqueous media due to their ability to quantitatively convert the metal ions to their zero oxidation state and concentrate the metal on and/or into the resin. The amount of metal present in the resultant metal containing resin can then be determined via gravimetric, spectroscopic or other analytical method and the microquantities of metal in the original volume of aqueous or non-aqueous media so treated can then be determined.

The ability of these resins to reduce ionic mercury salts and compounds and in particular methylmercury makes them especially useful in the detoxification of mercury polluted effluents.

Another area of application of the non-ionic borane reducing resins of the present invention is their use in the sugar refining industry as a decolorizing agent. In similar fashion these resins can be utilized as reducing agents for the removal of oxide impurities in chemicals such as alcohols, glycols, amines, amides and the like.

These reducing resins can also be utilized for reducing peroxides in peroxide forming organic compounds especially in ethers such as diethylether, tetrahydrofuran, diisopropyl ether and the like. These resins can be utilized in the removal of peroxides in ethers already contaminated with peroxides as well as being utilized as peroxide inhibitors in the storage or use of peroxide forming compounds.

The resins of this invention when impregnated with metals such as silver, copper, mercury, etc. can be employed in industrial applications as microbiocides in the textiles, paint, paper and laundry industries. These same resins can also find application in the removal of trace amounts of hydrogen sulfide, sulfur dioxide and the like from natural gas streams, coal gasification streams, coal and oil burning utility plants, sulfuric acid plants and the like. In these latter applications the potential high surface area of the finely divided, supported metal provides a high capacity material. The non-ionic borane reducing resins can also be utilized in elemental halogen and alkyl halide removal from aqueous and non-aqueous media via reduction to halide ion and an alkane respectively.

Certain of the non-ionic amine-borane reducing resins of this invention have applicability in organic synthesis procedures since the borane-resin adduct provides the desirable features that the reducing support is easily removed from the reaction mixture, the reduced material is attached to the resin system providing for complete separation of the product from the starting material. The reduced material can then be recovered from the resin by acid or base hydrolysis providing a pure product. The reducing support can then be chemically regenerated to the starting non-ionic amine borane reducing resin by procedures outlined above.

Another advantage of the borane reducing resins of this invention is their ability to provide a source of borane without the hazards associated with the use of this reagent. Another application for the amine-borane resins of the present invention is their use in the petroleum industry. Petroleum refining plants utilize noble metals as catalysts. These metals are presently recovered by dissolving them in aqua regia and then chemically reducing the metal chloride salts. However, the effluent from this process still contains about 10 to 15 ppm of metal ion. Anion exchange resins are presently used to remove these final trace amounts of metal. However, rhodium salts are not efficiently removed by anion exchange resins. Thus, the use of the high capacity amine-borane resins of the present invention can be used in place of the anion exchange resins in the above recovery process. The nonionic crosslinked resins containing amine or phosphine borane adducts can be advantageously employed in numerous applications as disclosed above. Other applications of these adducts which readily suggest themselves to those skilled in the art are meant to be included within the scope of the present specification and claims.

I claim:

1. A process for the removal of mercury, methyl mercury, antimony, arsenic, bismuth, silver, gold, palladium, platinum, rhodium, and iridium ions from aqueous and non-aqueous media which comprises contacting said media with a nonionic borane reducing resin which comprises a solid, cross-linked copolymer containing a plurality of amine- or phosphine-borane adduct functional groups, reducing the ions in solution by electron transfer and precipitating the reduced metals on and/or into the copolymer resin.

2. A process according to claim 1 wherein the amine- or phosphine-borane adduct functional group is of the formula

wherein $R^1$ and $R^2$ are independently
(a) hydrogen;
(b) ($C_1$–$C_8$) optionally substituted alkyl;
(c) ($C_6$–$C_{12}$) optionally substituted aryl; and
(d) ($C_7$–$C_{12}$) optionally substituted aralkyl; and
Z is nitrogen or phosphorous.

3. A process according to claim 2 wherein Z is nitrogen.

4. A process according to claim 1 wherein the solid, cross-linked copolymer containing a plurality of amine- or phosphine-borane adduct functional groups is of the formula

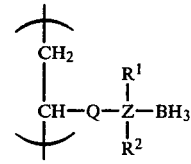

wherein Q is a group of the formula

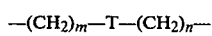

wherein m and n are independently integers from 0 to 3; and
T is the group

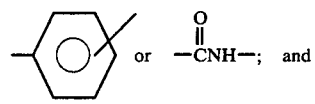

$R^1$ and $R^2$ are independently
(a) hydrogen;
(b) ($C_1$–$C_8$) optionally substituted alkyl;
(c) ($C_6$–$C_{12}$) optionally substituted aryl; and
(d) ($C_7$–$C_{12}$) optionally substituted aralkyl; and Z is nitrogen or phosphorous.

5. A process according to claim 4 wherein Z is nitrogen.

6. A process according to claim 5 wherein $R^1$ and $R^2$ are independently hydrogen, ($C_1$–$C_8$) unsubstituted alkyl, ($C_6$–$C_{12}$) unsubstituted aryl or ($C_7$–$C_{12}$) unsubstituted aralkyl.

7. A process according to claim 6 wherein T is the group

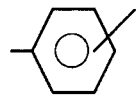

8. A process according to claim 7 wherein $R^1$ and $R^2$ are independently hydrogen, ($C_1$–$C_4$) unsubstituted alkyl or unsubstituted phenyl, biphenyl, benzyl or phenethyl.

9. A process according to claim 8 wherein the resin is in a macroreticular form.

10. A process according to claim 9 wherein the metal ions are selected from the group consisting of mercury, methyl mercury, silver, gold, platinum, antimony, arsenic and bismuth ions.

* * * * *

UNITED STATES PATENT AND TRADEMARK OFFICE
CERTIFICATE OF CORRECTION

PATENT NO. : 4,240,909
DATED : December 23, 1980
INVENTOR(S) : Larry Manziek

It is certified that error appears in the above—identified patent and that said Letters Patent is hereby corrected as shown below:

Column 1, line 15 -- Gasparini

Column 1, line 31 -- stabile

Column 4, line 68 -- borane

Column 7 and Column 8 table

| Metal ion | Source | Not Reduced | Reduced |
|---|---|---|---|
| $Na^+$ | NaCl | ✓ | - |
| $K^+$ | KCl | ✓ | - |
| $Li^+$ | LiCl | ✓ | - |
| $Mg^{+2}$ | $MgCl_2$ | ✓ | - |
| $Ca^{+2}$ | $CaCl_2$ | ✓ | - |
| $Cr^{+3}$ | $CrCl_3$ | ✓ | - |
| $Cr^{+6}$ | $K_2Cr_2O_6$ | ✓ | - |

UNITED STATES PATENT AND TRADEMARK OFFICE
CERTIFICATE OF CORRECTION

PATENT NO. : 4,240,909

DATED : December 23, 1980

INVENTOR(S) : Larry Manziek

Page 2 of 3

It is certified that error appears in the above—identified patent and that said Letters Patent is hereby corrected as shown below:

| Metal ion | Source | Not Reduced | Reduced |
|---|---|---|---|
| $UO_2^+$ | $UO_2NO_3$ | ✓ | – |
| $Bi^{+3}$ | $Bi(NO_3)_3$ | – | ✓ |
| $As^{+3}$ | $As_2O_3$ | – | ✓ |
| $Mn^{+2}$ | $MnCl_2$ | ✓ | – |
| $Fe^{+2}$ | $FeCl_2$ | ✓ | – |
| $Fe^{+3}$ | $FeCl_3$ | ✓ | – |
| $Co^{+2}$ | $CoCl_2$ | ✓ | – |
| $Ni^{+2}$ | $NiCl_2$ | ✓ | – |
| $Cu^{+2}$ | $CuCl_2$ | ✓ | – |
| $Zn^{+2}$ | $ZnCl_2$ | ✓ | – |
| $Rh^{+3}$ | $RhCl_3$ | – | ✓ |

UNITED STATES PATENT AND TRADEMARK OFFICE
CERTIFICATE OF CORRECTION

PATENT NO. : 4,240,909
DATED : December 23, 1980
INVENTOR(S) : Larry Manziek

It is certified that error appears in the above—identified patent and that said Letters Patent is hereby corrected as shown below:

| Metal ion | Source | Not Reduced | Reduced |
|---|---|---|---|
| $Pd^{+2}$ | $PdCl_2$ | – | ✓ |
| $Ag^{+1}$ | $AgNO_3$ | – | ✓ |
| $Cd^{+2}$ | $CdCl_2$ | ✓ | – |
| $Ir^{+3}$ | $IrCl_3$ | – | ✓ |
| $Pt^{+4}$ | $H_2PtCl_6$ | – | ✓ |
| $Au^{+3}$ | $HAuCl_4$ | – | ✓ |
| $Hg^{+2}$ | $HgCl_2$ | – | ✓ |
| $Sb^{+3}$ | $Sb_2O_3$ | – | ✓ |
| $Sr^{+2}$ | $SrCl_2$ | ✓ | – |
| $Pb^{+2}$ | $PbCl_2$ | ✓ | – |
| $Tl^{+1}$ | $Tl_2(SO_4)$ | ✓ | – |
| $Pb^{+4}$ | $Et_4Pb$ | ✓ | – |
| $CH_3Hg^+$ | $CH_3HgCl^-$ | – | ✓ |

Signed and Sealed this

Sixth Day of December 1983

[SEAL]

Attest:

GERALD J. MOSSINGHOFF

Attesting Officer    Commissioner of Patents and Trademarks